United States Patent [19]

Niiyama et al.

[11] Patent Number: 4,579,642
[45] Date of Patent: Apr. 1, 1986

[54] ELECTROCHEMICAL SENSOR HAVING AN IMMOBILIZED ENZYME MEMBRANE

[75] Inventors: Yasusi Niiyama, Katsuta; Junji Mori, Hitachi; Kenshi Sugahara, Katsuta, all of Japan

[73] Assignee: Hitachi, Ltd., Tokyo, Japan

[21] Appl. No.: 668,891

[22] Filed: Nov. 7, 1984

[30] Foreign Application Priority Data

Nov. 8, 1983 [JP] Japan .................................. 58-209684

[51] Int. Cl.[4] .......................... C12Q 1/00; C12Q 1/58; G01N 27/30
[52] U.S. Cl. ..................................... 204/403; 435/291; 435/817
[58] Field of Search ................ 204/403, 1 E; 435/817, 435/291

[56] References Cited

U.S. PATENT DOCUMENTS 4,224,125  9/1980  Nakamura et al. .............. 435/817 X
4,476,005 10/1984  Tokinaga et al. ................... 204/403

OTHER PUBLICATIONS

G. G. Guilbault et al., Anal. Chem., vol. 45, No. 2, pp. 417-419, (1973).

*Primary Examiner*—G. L. Kaplan
*Attorney, Agent, or Firm*—Antonelli, Terry & Wands

[57] ABSTRACT

A recess of a predetermined thickness is formed in the bottom of a cylindrical vessel and a hole for the liquid-junction is formed at the center of the recess, to which is joined a resilient $NH_4^+$ selective membrane. Since the $NH_4^+$ selective membrane has a thickness larger by about 0.1 mm than the depth of the recess, the $NH_4^+$ selective membrane is protruded out of the bottom of the vessel by so much. A polyester woven fabric on which urease is immobilized is attached to the vessel so as to cover the $NH_4^+$ selective membrane. Since the immobilized enzyme membrane is applied with an appropriate tension by the slightly protruded ion selective membrane, bondability between the two membranes can be improved.

12 Claims, 10 Drawing Figures

ELECTROCHEMICAL SENSOR HAVING AN IMMOBILIZED ENZYME MEMBRANE

BACKGROUND OF THE DISCLOSURE

This invention concerns an electrochemical sensor having an immobilized enzyme membrane and, more specifically, it relates to an electrochemical sensor suitable to the measurement of ingredients contained in living body fluids by utilizing enzyme catalyzed reactions.

It has become more and more important in doctor's diagnosis and therapy for patients, as well as in various other fields to measure or monitor the concentration of various substances such as urea, glucose and amino acids contained in living body fluids.

In view of the above, various types of enzyme electrodes comprising various ion selective electrodes or gas electrodes and immobilized enzymes in combination have been developed in order to conduct such measurement with ease and rapidity. The analysis using these enzyme electrodes has many advantages as compared with the conventional colorimetric method in that the structure of the measuring device is simplified, the time required for the analysis is shorter and the analysis can be made on a smaller amount of specimen.

For instance, a urea electrode comprises a combination of an ammonium ion electrode and an immobilized urease membrane, with which the following reactions are carried out.

In this enzyme electrode, urea contained in the blood is decomposed by urease, and ammonia as the decomposition product (hereinafter referred to as $NH_3$) is detected by a $NH_3$ gas electrode or detected, after being converted into ammonium ions (hereinafter referred to as $NH_4^+$) by a $NH_4^+$ selective electrode, in which the urea concentration in the blood indispensable for the diagnosis of nephrosis or the like can be calculated based on the potential change at the electrode.

An example of the urea electrode is disclosed, for instance, in *Analytical Chemistry*, vol. 45, No. 2 p 417 (1973). In this example, the ammonium ion selective electrode has on its surface a thin immobilized urease layer. In such an enzyme electrode, while the $NH_4^+$ selective membrane and the immobilized urease membrane are merely overlapped with each other, good bondability is not obtainable between the two membranes and, further, high responsivity can not be obtained.

Since the conventional enzyme electrode comprising the combination of the ion selective electrode and the immobilized enzyme membrane has a drawback in the response time as described above and although it can be used in combination with a batch type measuring cell in which no severe conditions are required for the analysis cycle, it can not be applied to the rapid and continuous measurement of specific chemical substances contained in living body fluids while being incorporated in a flow type measuring cell.

SUMMARY OF THE INVENTION

Accordingly, it is an object of this invention to provide an electrochemical sensor having an excellent responsivity.

Another object of this invention is to provide an enzyme electrode that can be used as a sensor also in the flow analysis method.

In this invention, a vessel having a liquid-junction is formed at the end face thereof with a recess of a predetermined depth, to which a resilient ion selective membrane is secured. The thickness of the ion selective membrane is larger than the depth of the recess. Accordingly, the ion selective membrane slightly protrudes out of the end face of the vessel. The surface of the ion selective membrane is covered with an immobilized enzyme membrane.

With such a structure, an intense bondability can be obtained between the two membranes due to the resiliency of the ion selective membrane. Further, an ion selective membrane of a smaller area can be mounted to thereby improve the responsivity.

DETAILED DESCRIPTION OF THE PREFERRED EMBODIMENT

Figure 1:
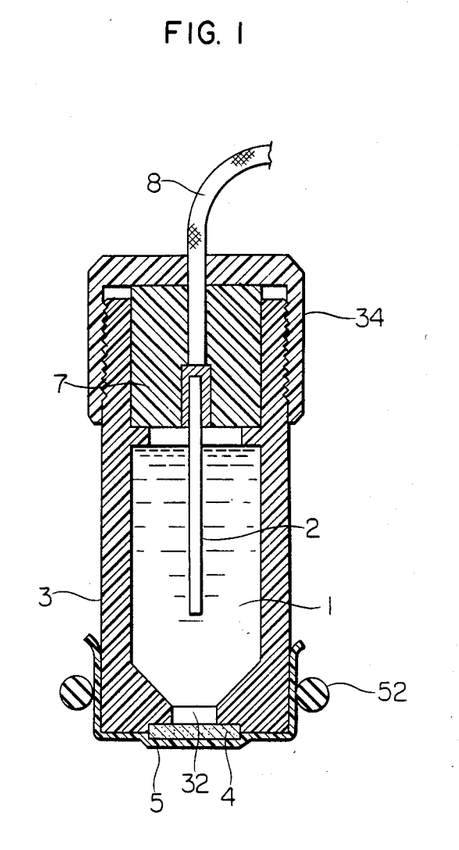
FIG. 1 is a schematic cross sectional view for the structure of an urea electrode as one embodiment according to this invention.

Referring to FIG. 1, inner electrolyte 1 is contained within a cylindrical vessel 3 made of polyvinyl chloride and an inner electrode wire 2 is immersed in the electrolyte 1. The wire 2 is connected to a lead wire 8. An insulating plug 7 for holding the wire 2 covers the upper portion of the vessel 3 and is plugged tightly by a cap 34. The vessel 3 opens at the bottom as a liquid-junction 32, which forms a hole of a diameter smaller than the inner diameter of the vessel 3, through which an ammonium ion selective membrane 4 is in direct contact with the electrolyte 1. The $NH_4^+$ selective membrane 4 is joined within a facing hole formed in the bottom of the vessel 3. The surface of the $NH_4^+$ selective membrane 4 and the end face of the vessel 3 are covered with a thin polyester woven fabric 5 having an immobilized enzyme membrane. The fabric 5 having the urease membrane is retained by means of a rubber ring 52 to the vessel 3.

The urea electrode shown in FIG. 1 is manufactured as described below. At first, a facing hole is recessed to the bottom of the polyvinyl chloride (PVC) vessel formed with the liquid-junction 32. The facing hole formed at the bottom is coaxial with the center of the liquid-junction and is 3 mm in diameter and 0.2 mm in depth. The vessel 3 has an outer diameter of 10 mm and an inner diameter of 6 mm with the liquid-junction 32 having a diameter of 1.5 mm.

The $NH_4^+$ selective membrane 4 of 3 mm in diameter and 0.3 mm in thickness is secured in the facing hole using an organic solvent tetrahydrofuran (hereinafter referred to THF). The $NH_4^+$ selective membrane 4 is prepared as a membrane using polyvinyl chloride as the matrix, dioctyl adipate (hereinafter referred to as DOA) as a plasticizer and antibiotic Nonactin as a sensitive substance mixed with each other. The membrane 4 has a resiliency. Since the vessel 3 and the matrix for the $NH_4^+$ selective membrane 4 are made of the same material, that is, polyvinyl chloride, various advantages can be obtained in that the vessel 3 and the $NH_4^+$ selective membrane 4 can be integrated to each other without using such an adhesive that will give undesired effects on the characteristics of the membrane 4, an increase in the leak current due to the intrusion of adhesives into the gap or the like during long time of use can be suppressed as much as possible and the electrode can be the manufactured easily and rapidly.

The $NH_4^+$ selective membrane 4 protrudes by about 0.1 mm from the end face of the vessel 3 after being secured thereto. Then, the polyester woven fabric 5 is attached so as to cover the surface of the $NH_4^+$ selective membrane 4 and the end face of the vessel 3. An immobilized urease membrane is formed on the part of the polyester woven fabric 5 that corresponds to the $NH_4^+$ selective membrane 4. The plane size of the urease membrane is slightly larger than that of the $NH_4^+$ selective membrane 4 so as to completely cover the latter. Specifically, an immobilized urease membrane 6 mm in diameter and 0.04 mm in thickness is prepared by crosslinking to immobilize urease and albumin with gltaraldehyde on a polyester fabric as a support. The polyester fabric is less swollen to water and less changes in the tensile strength in liquid. The polyester fabic 5 is placed on a table and secured to the vessel 3 in a state where the $NH_4^+$ selective membrane 4 is urged to the end face of the vessel 3 so that the end face of the vessel 3 is flush with the surface of the $NH_4^+$ selective membrane 4. In the urea electrode thus completed, the polyester fabric 5 is urged by an appropriate force by the resiliency of the $NH_4^+$ selective membrane 4.

Then, 0.1M $NH_4Cl$ solution as the inner electrolyte 1 and an Ag/AgCl electrode as the inner electrode 2 are sealed into the vessel 3 and the plug 7 and the lead wire 8 are connected to constitute the urea electrode.

As described hereinafter, the responsivity of the enzyme electrode corresponding to the concentrations of measuring items in the sample liquid can significantly be improved in the embodiment shown in FIG. 1, because a good bondability can be attained between the ion selective membrane and the immobilized enzyme membrane, and the diameter for the ion selective membrane can be minimized as compared with the effective diameter of the liquid-junction in communication with the inner electrolyte. Further, since the bondability between the two membranes can now be maintained for a long time, the working life of the enzyme electrode can be improved.

The facing hole formed in the bottom of the vessel 3 is effective for decreasing the size of the ion selective membrane. The size of the facing hole is smaller than the inner diameter of the vessel 3 but sufficiently larger than the bore diameter for the liquid-junction 32 to ensure the bonding strength of the ion selective membrane. Upon preparing the enzyme electrode, the resilient ion selective membrane 4 is secured in the facing hole and, thereafter, the immobilized enzyme membrane 5 having a certain tensile strength is bonded under pressure on the acting surface of the thus secured ion selective membrane 4 such that it is in flush with the end face of the outer tube 3 followed by securing, whereby the bondability between both of the membranes 4 and 5 can be maintained for a long period of time owing to the resiliency of the ion selective membrane 4 bonded under pressure.

The height of the surface of the ion selective membrane 4 protruding out of the end face of the vessel 3 is adequately between 1/100-1/10 of the diameter of the ion selective membrane 4. Although the immobilized enzyme membrane may be formed over the entire region of the polyester fabric 5, since the enzyme catalyzed reaction occurs in this case at the area substantially equal to that of the bottom face of the vessel 3, the responsivity characteristic is reduced as the area of the bottom is larger. Accordingly, in the case of disposing the immobilized enzyme membrane over the entire region of the polyester fabric, some adequate measure may be taken for decreasing the area on the bottom of the vessel.

Figure 2:
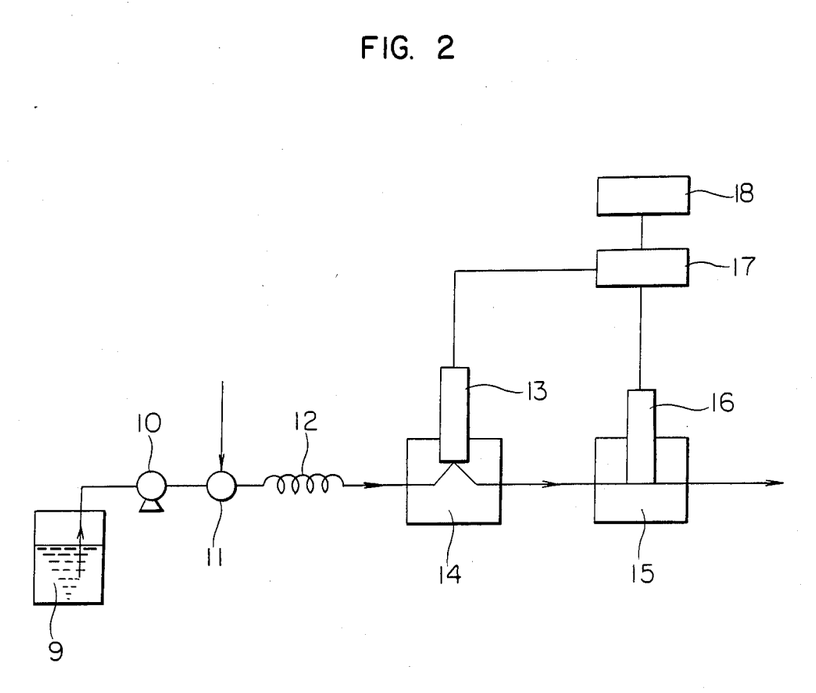
FIG. 2 is a schematic view illustrating the line of a flow analyzer disposed with the sensor shown in FIG. 1.

In FIG. 2, the flow type measuring system comprises a buffer solution 9 as a carrier for the measured sample, a peristaltic pump 10, a sample injector 11, a mixing coil 12, a urea electrode 13, a flow type urea electrode measuring cell 14, a reference electrode cell 15, a reference electrode 16, an amplifier 17 and a recorder 18. In the measuring system, 10 µl of sample are injected by means of a microsyringe from the sample injector 11 into the buffer solution 9 flowing at the rate of 2.0 ml/min, and the sample is diluted within the mixing coil 12. When the diluted sample arrives at the acting surface of the urea electrode, the change in the potential resulted on the electrode can be read by the recorder 18.

Figure 3:
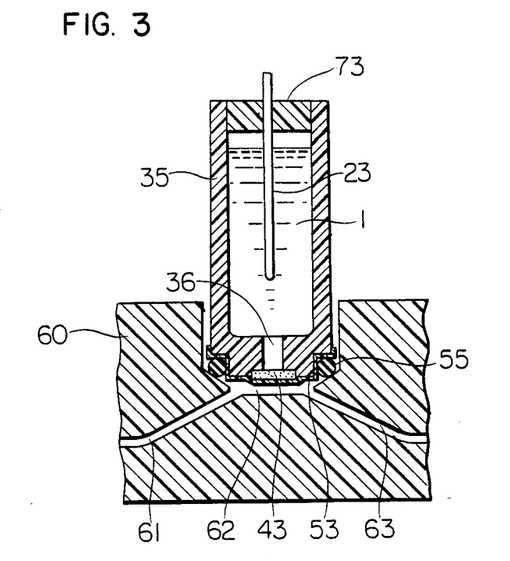
FIG. 3 is a schematic cross sectional view for the structure of another embodiment according to this invention.

FIG. 3 shows another embodiment according to this invention, in which an enzyme electrode with a reduced end face area is attached in a flow cell. The vessel 35 shown in FIG. 3 has larger and smaller outer diameter portions. The smaller outer diameter portion is provided so as to reduce the area for the bottom of the vessel 35. The outer diameter of the vessel 35 is 10 mm at the larger portion and 6 mm at the smaller portion. The facing hole formed below a liquid-junction 36 is 3 mm in diameter and 0.2 mm in depth. The $NH_4^+$ selective membrane 43 is 3 mm in diameter and 0.3 mm in thickness. A circular immobilized urease membrane about 6 mm in diameter is formed on a polyester woven fabric 53, and the fabric 53 is retained by means of a rubber ring 55 such that the portion thereof for the immobilized urea membrane agrees with the bottom surface of the vessel 35. An inner electrode 23 held by a plug 73 is immersed in an electrolyte 1.

In a flow cell main body 60 shown in FIG. 3, are formed an inlet channel 61 and an outlet channel 63 for flowing a carrier liquid and a sample liquid, which are joined to form a dish-like measuring portion 62. The urea electrode is inserted in this measuring portion 62 and attached such that there may be an appropriate gap maintained between the surface of the immobilized enzyme membrane 53 and the bottom face of the measuring portion 62. The inside of the flow cell is kept sealed by a rubber ring 55 so as to prevent liquid leakage.

In the structure either of FIG. 1 or FIG. 3, degradation in the bondability between the ion selective membrane 4 and the immobilized enzyme membrane 5 caused by the leaching of the plasticizer contained in the ion selective membrane during long time use can be minimized, as well as increase in the diameter of the ion selective membrane 4 and the gap resulted between the outer tube 3 and the immobilized enzyme membrane 5 can be restricted to minimum. Accordingly, there are less degradation in the responsive characteristic and the drift due to the stagnation of the measured fluid and an enzyme electrode of an improved life having a slope voltage approximately to that of the theoretical level can be obtained. Furthermore, the enzyme electrode thus obtained has a high response speed, if particularly suitable for use in the flow type measuring cell and can be manufactured with ease.

Figure 4:
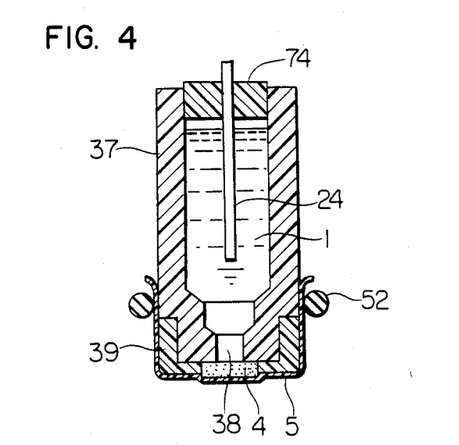
FIG. 4 is a schematic cross sectional view showing the structure of a further embodiment according to this invention.

In the embodiment shown in FIG. 4, an electrically insulating vessel is constituted with a cylinder main body 37 having larger and smaller outer diameter portions and a retaining ring 39 joined with each other. An ion selective membrane 4 is in contact with the end of a liquid-junction 38 and contained in the through hole of the retaining ring 39. The surface of the ion selective membrane 4 protrudes by about 0.1 mm from the end face of the retaining ring 39. The end face of the retaining ring 39 forms the end face of the vessel in this embodiment. An inner electrode 24 is held by a plug 74.

Figure 5:
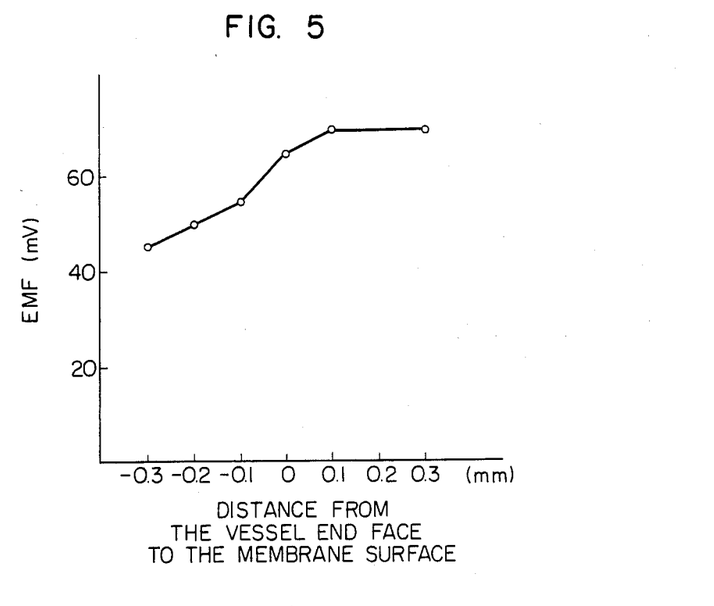
FIG. 5 is a graph showing the relationship between an output voltage and the distance from the end face of the vessel to the surface of the $NH_4^+$ selective membrane.
Figure 6:
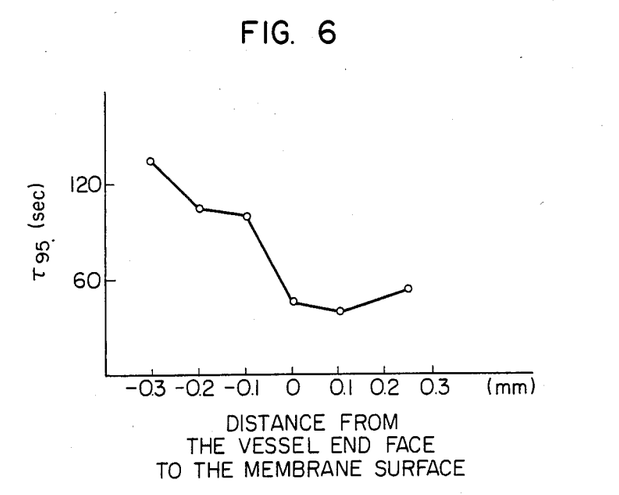
FIG. 6 is a graph showing the relationship between the response time and the distance from the surface of the vessel to the surface of the $NH_4^+$ selective membrane.

FIG. 5 and FIG. 6 show the data of the experiment in which an electrode with the same structure as that in FIG. 1 was used and the depth of the facing hole was changed so as to examine the effect caused by the variation of the distance from the end face of the vessel to the surface of the ion selective membrane on the output of the electrode. The abscissa in each of FIG. 5 and FIG. 6 indicates the distance from the end face of the vessel to the surface of the $NH_4^+$ selective membrane. The negative value in the distance means that the end face of the vessel is higher. The ordinate in FIG. 5 indicates the electromotive force (EMF) and the ordinate in FIG. 6 indicates the response time $\tau 95$ required to reach 95% of the output where it is completely stabilized.

As can be seen from FIG. 5 and FIG. 6, in the illustrated case where the ion selective membrane has a diameter of 3 mm and the end face of the vessel has a diameter of 10 mm, both of the output voltage and the response speed are most preferred when the $NH_4^+$ selective membrane 4 is secured with a protrusion by about 0.1 mm from the end face of the outer tube 3. In this case, although the initial characteristic is satisfactory and the desired bondability between the two membranes can be secured to some extent where the $NH_4^+$ selective membrane 4 is secured on the same plane with the end face of the vessel 3, the bondability between the two membranes is reduced due to the retraction and shrinkage of the $NH_4^+$ selective membrane 4 caused by the leaching of DOA during long time use and accompanying degradation was observed in the responsive characteristic.

Figure 7:
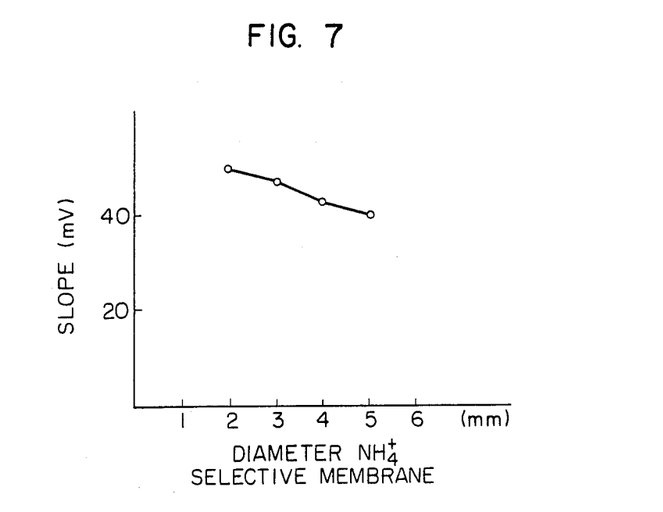
FIG. 7 is a graph showing the relationship between the slope output and the diameter of the $NH_4^+$ selective membrane.

Further, if the $NH_4^+$ selective membrane 4 protrudes excessively, the manufacture becomes difficult, as well as change in the composition of the membrane is promoted due to the excess force applied to the $NH_4^+$ selective membrane 4, tending to cause degradation in the working life. Accordingly, it is desired that the protruding length is not so large. Then, with respect to the relationship between the membrane diameter and the responsive characteristic of the $NH_4^+$ selective membrane 4, it can be seen as illustrated in FIG. 7 that the responsive characteristic is better as the membrane diameter is smaller, provided that reasonable size can be secured for the liquid-junction and for the bonding area 43.

The urea electrode formed in such a structure that the bondability between the $NH_4^+$ selective membrane 4 and the immobilized urease membrane 5 is maintained by utilizing the resiliency of the $NH_4^+$ selective membrane 4 can provide a significantly improved responsive characteristic with the responsive time $\tau 95$ being within 60 sec and can operate satisfactorily for the continuous use when it is incorporated into the flow type measuring cell as compared with the conventional electrode.

Figure 8:
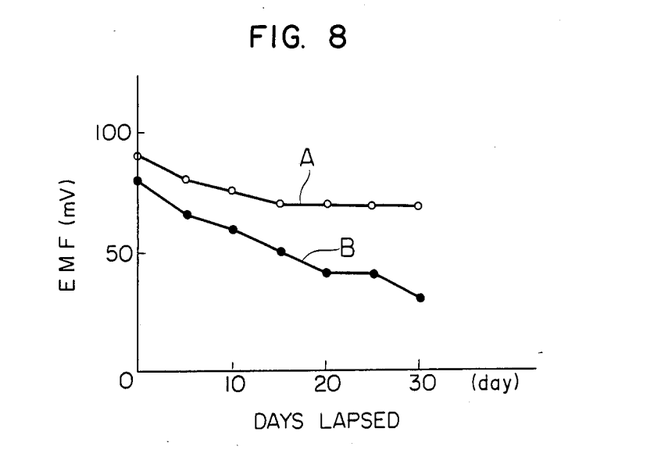
FIG. 8 is a graph showing the change with time in the output of the urea electrode according to this invention and of the conventional urea electrode.

In FIG. 8, data A show the change with time in the urea electrode according to this invention and data B show the change with time in the conventional urea electrode in which the ion selective membrane and the immobilizied enzyme membrane are merely overlaid with each other. According to this invention, the fluctuation in the electromotive force is descreased and the working life is improved.

Figure 9:
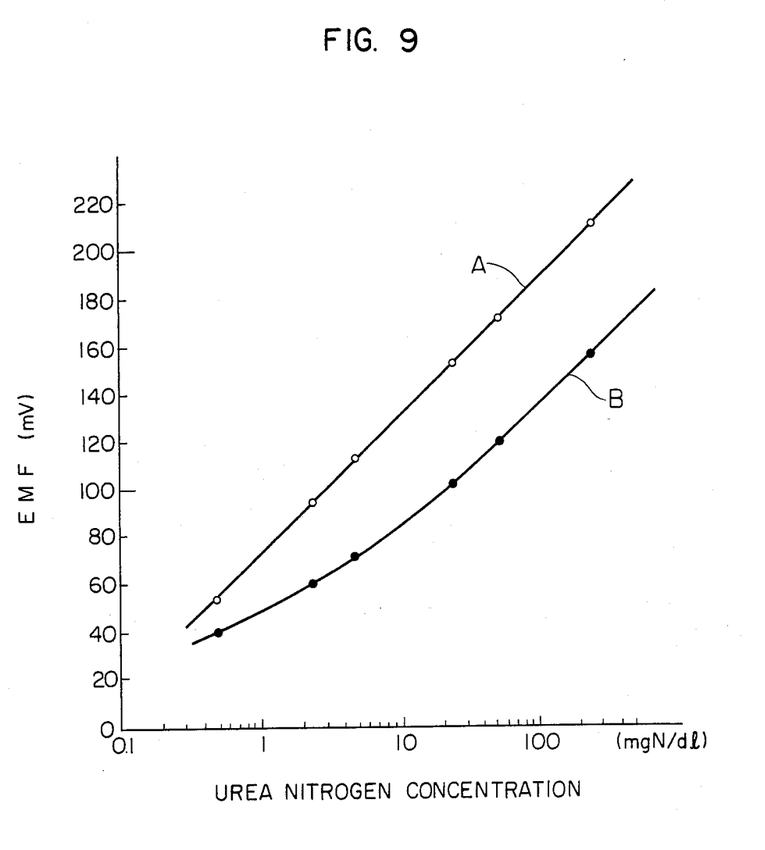
FIG. 9 is a graph showing the linearity on the calibration curves of the urea electrode according to this invention and of the conventional urea electrode.

Further, with respect to the calibration curve giving a significant effect on the measuring accuracy, it was confirmed that the electrode according to this invention could ensure the linearity over a region between 5–30 mgN/dl which is the concentration of urea nitrogen in the blood of healthy persons, which was difficult so far by the conventional enzyme electrode, and exhibited the characteristic of a logarithm function of a sufficient linearity for the region between 1–300 mgN/dl in the urea nitrogen concentration as shown by the curve A in FIG. 9 as compared with that of the conventional electrode shown by the curve B and particularly could improve the measuring accuracy outstandingly at the low concentration region, which was considered difficult so far. Furthermore, the thus obtained urea electrode 8 shown satisfactory characteristic, in view of the correlation with the indicated values of the commercial control serum (by way of colorimetry), as: correlation coefficient of 0.982, $y=0.96\times +2.0$ (n=12), fluctuation coefficient of 1.4% in the simultaneous reproducibility, 70 mgN/dl+1 mgN/dl (n=10). Particularly, when the electrode according to this invention is combined with the flow type measuring cell, it provides an extremely useful effect upon measuring the urea concentration in the patient's blood continuously and rapidly.

Figure 10:
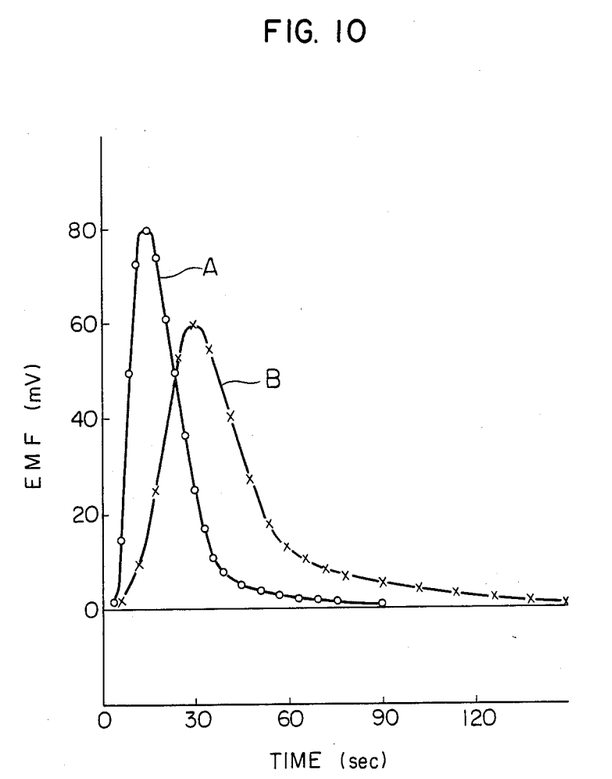
FIG. 10 is a graph showing the response time of the urea electrode according to this invention and of the conventional urea electrode.

FIG. 10 shows the result of the comparison for the response speed between the urea electrode according to this invention and the conventional urea electrode. The response speed shown by the data A according to this invention is about twice as high as the response speed shown by the data B of the conventional electrode.

As apparent from the foregoing explanation, according to this invention, since the membrane diameter of the ion selective membrane is made smaller and the bondability between the ion selective membrane and the immobilized enzyme membrane can be maintained for a long time by utilizing the resiliency of the ion selective membrane, extremely useful effects can be attained in that the manufacture of the electrode can be simplified, the responsive characteristic and the working life can be improved and, particularly, continuous measurement of the sample concentration is enabled in combination with the flow type measuring cell.

What is claimed is:

1. An electrochemical sensor which comprises a vessel formed with a liquid-junction at an end face of the vessel, a resilient ion selective membrane disposed at the liquid-junction, and an immobilized enzyme membrane arranged to cover said ion selective membrane; a recess of a predetermined depth being formed in the end face of said vessel and the resilient ion selective membrane having a thickness larger than the depth of said recess; said ion selective membrane being secured to said recess and pressed therein by the immobilized enzyme membrane.

2. The electrochemical sensor according to claim 1, wherein the ion selective membrane is a circular member with one surface contacting the end face of the vessel and other surface protruding from the recess; the other surface of the ion selective membrane protruding from the end face of the vessel for a distance between 1/100–1/10 of the diameter of said ion selective membrane.

3. The electrochemical sensor according to claim 1, wherein the material forming the vessel is the same material as that forming a matrix portion of the ion selective membrane.

4. The electrochemical sensor according to claim 1, wherein the immobilized enzyme membrane is formed on a polyester woven fabric.

5. An electrochemical sensor comprising a vessel means having a liquid-junction opened at the bottom end face of the vessel means; a recess formed in the end face of said vessel means and in communication with said liquid-junction, a resilient ion selective membrane arranged partially in said recess, the membrane having substantially the same plane size as that of said recess and a thickness larger than the depth of said recess, and an immobilized enzyme membrane less swollen to water covering said ion selective member to urge said ion selective membrane against said recess.

6. The electrochemical sensor according to claim 5, wherein said vessel contains an ammonium salt solution as electrolyte, the ion selective membrane is an ammonium ion selective membrane and the immobilized enzyme membrane is an immobilized urease.

7. The electrochemical sensor as defined in claim 5, wherein the vessel means comprises a cylindrical member and the ion selective membrane is a circular flat member, the diameter of the ion selective membrane being smaller than an inner diameter of the cylindrical member.

8. The electrochemical sensor according to claim 5, wherein the cylindrical member of the vessel means has a larger outer diameter portion and a smaller outer diameter portion, the vessel end face being formed at the smaller outer diameter portion.

9. An electrochemical sensor comprising a cylindrical vessel containing an electrolyte and having an opening at one end face forming a liquid-junction, a recess formed in the end face and in communication with said liquid-junction; a resilient ion selective membrane located partially within said recess, and an immobilized enzyme membrane arranged to cover the end face of the vessel and to press the ion selective membrane against the recess; said ion selective membrane having a thickness that is greater than the depth of the recess so that a surface of the ion selective membrane protrudes from the end face of the vessel and said immobilized enzyme membrane comprising a woven fabric which intimately contacts the protruding surface of the ion selective membrane whereby good bondability is provided between the ion selective membrane and the immobilized enzyme membrane.

10. The electrochemical sensor according to claim 9, wherein said vessel contains an ammonium salt solution as electrolyte, the ion selective membrane is an ammonium ion selective membrane and the immobilized enzyme membrane is an immobilized urease.

11. The electrochemical sensor according to claim 9, wherein the ion selective membrane is a circular member with one surface contacting the end face of the vessel and other surface protruding from the recess; the other surface of the ion selective membrane protruding from the end face of the vessel for a distance between 1/100–1/10 of the diameter of said ion selective membrane.

12. The electrochemical sensor according to claim 9, wherein the vessel is formed of polyvinyl chloride, the ion selective membrane comprises a matrix made of polyvinyl chloride, and the woven fabric of the immobilized enzyme membrane comprises a polyester.

* * * * *